United States Patent [19]

James

[11] Patent Number: 4,748,245

[45] Date of Patent: May 31, 1988

[54] PROCESS FOR MAKING PHENYLTHIOPYRIMIDINES

[75] Inventor: Donald R. James, El Sobrante, Calif.

[73] Assignee: Stauffer Chemical Company, Westport, Conn.

[21] Appl. No.: 841,964

[22] Filed: Mar. 20, 1986

[51] Int. Cl.$^4$ .............. C07D 239/38; C07D 239/56; C07D 403/12

[52] U.S. Cl. .................... 544/316; 544/300; 544/301; 544/302; 544/310; 544/312; 544/313; 544/314; 544/317; 544/318

[58] Field of Search ............ 544/318, 300, 301, 302, 544/310, 312, 313, 314, 316, 317

[56] References Cited

U.S. PATENT DOCUMENTS 4,248,618  2/1981  Serban et al. ................ 544/318
4,427,437  1/1984  Serban et al. ................ 544/318

Primary Examiner—Richard A. Schwartz
Assistant Examiner—Kurt G. Briscoe
Attorney, Agent, or Firm—Paul R. Martin; Joel G. Ackerman

[57] ABSTRACT

A process for the preparation of phenylthiopyrimidines which comprises: (a) reacting a thiopyrimidine; with sulfuryl chloride in the presence of a suitable solvent to form the sulfenyl chloride of said thiopyrimidine; (b) reacting said sulfenyl chloride of said thiopyrimidine with a phenol or substituted phenol, optionally in the presence of a Friedal-Crafts catalyst, to form a thiopyrimidinyl phenol; and (c) reacting said thiopyrimidinylphenol formed in step (b) with a base and an alkylating agent to form the end product.

9 Claims, No Drawings

PROCESS FOR MAKING PHENYLTHIOPYRIMIDINES

BACKGROUND OF THE INVENTION

The present invention relates to a process for making phenylthiopyrimidines. Phenylthiopyrimidines are useful as herbicides, representative ones of which are described and claimed in commonly assigned U.S. patent application Ser. Nos. 774,212 and 755,111. These compounds have been found to have good herbicidal activity when applied postemergent against a number of weed species.

THE PRIOR ART

The phenylthiopyrimidine compounds of this invention have not been previously known in the art, nor a process for making them. The closest compounds thereto are heterocyclic thio-substituted phenyl N-alkyl carbamates and thiolcarbamates which are disclosed in British Pat. No. 1,447,428.

DESCRIPTION OF THE INVENTION

A process for the preparation of phenylthiopyrimidines has now been discovered which comprises:

(a) reacting a thiopyrimidine of the formula

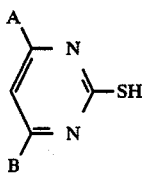

wherein A and B are the same or different and are selected from the group consisting of hydrogen, straight or branched chain alkyl groups having from 1 to about 5 carbon atoms, alkoxy wherein the alkyl group has from 1 to about 5 carbon atoms, mono- or di-alkyl substituted amine wherein the alkyl group has from 1 to about 5 carbon atoms, cyano, COO-alkyl wherein the alkyl group has from 1 to about 5 carbon atoms, trifluoromethyl, chlorine or fluorine; with a sulfuryl chloride chlorinating agent in the presence of a halocarbon solvent to form the sulfenyl chloride of said thiopyrimidine;

(b) reacting said sulfenyl chloride of said thiopyrimidine with phenol or an substituted phenol of the formula

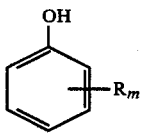

wherein R is hydrogen, alkyl having from 1 to about 5 carbon atoms, halogen, phenyl, cyano, COO-alkyl wherein the alkyl group has from 1 to about 5 carbon atoms, trifluoromethyl or alkoxy wherein the alkyl group has from 1 to about 5 carbon atoms; and m is an integer of from 1 to 4; optionally in the presence of a Friedal-Crafts catalyst, preferably aluminum chloride, to form a thiopyrimidinylphenol of the formula

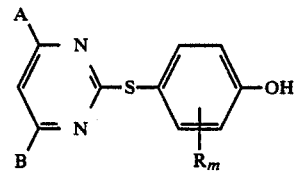

wherein A, B and $R_m$ are as defined above; and (c) reacting said thiopyrimidinylphenol formed in step (b) with a base and an alkylating agent of the formula $R'-X_a$ wherein R' is a straight or branched chain alkyl group having from 1 to about 5 carbon atoms, an arylalkyl moiety of the formula

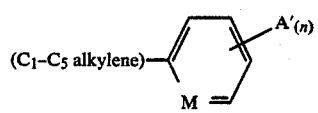

wherein the alkylene group is straight or branched chain; A' is selected from the group consisting of hydrogen, halogen, straight or branched chain alkyl having from 1 to about 5 carbon atoms, nitro, cyano, methoxy, halogenated alkyl having from 1 to about 5 carbon atoms and ester groups, wherein n is an integer from 1 to 5; M is CH or nitrogen; and $X_a$ is chlorine, bromine or iodine, to form

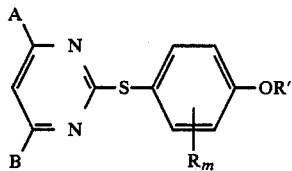

wherein A, B, $R_m$ and R' are as defined above.

The term "alkyl" as used herein refers to non-cyclic saturated hydrocarbon radicals which may be straight or branched chain. Examples include methyl, ethyl, propyl, isopropyl, butyl, isobutyl, pentyl, etc.

The compounds produced in accordance with the method of this invention therefore comprise phenylthiopyrimidines of the formula

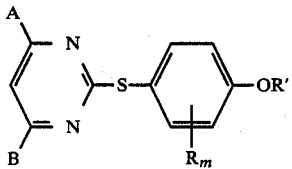

wherein A and B are the same or different and are selected from the group consisting of hydrogen, straight or branched chain alkyl groups having from 1 to about 5 carbon atoms, alkoxy having from 1 to about 5 carbon atoms, mono- or di-alkyl substituted amine wherein the alkyl group has from 1 to about 5 carbon atoms, cyano, COO-alkyl wherein the alkyl has from 1 to about 5 carbon atoms, trifluoromethyl, chlorine or fluorine; R is hydrogen, alkyl having from 1 to about 5 carbon atoms, halogen, phenyl, cyano, COO-alkyl wherein the alkyl group has from 1 to about 5 carbon atoms, trifluoromethyl or alkoxy wherein the alkyl group has from 1 to about 5 carbon atoms; m is an integer of from 1 to 4; and R' is a straight or branched chain alkyl group having from 1 to about 5 carbon atoms, or a arylalkyl moiety of the formula

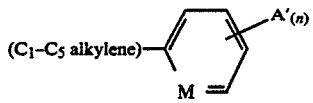

wherein the alkylene group is straight or branched chain; A' is selected from the group consisting of hydrogen, halogen, straight or branched chain alkyl having from 1 to about 5 carbon atoms, nitro, cyano, methoxy, halogenated alkyl and ester groups wherein the alkyl group has from 1 to about 5 carbon atoms, wherein n is an integer from 1 to 5, and M is CH or nitrogen.

The process of this invention will be more fully understood by reference to the following examples, which are intended to be illustrative of the process but not limiting thereof.

EXAMPLE 1

Preparation of 2-[3-chloro-4-(3-trifluoromethylphenylmethoxy)]phenylthio 4,6-dimethyl pyrimidine A 100 milliliter (ml) round-bottom flask equipped with a stir bar and drying tube was charged with 5 grams (g) of 2-mercapto-4,6-dimethylpyrimidine in dry methylene chloride. Then one equivalent (4.8 g) of sulfuryl chloride was added portion-wise and the solution was stirred for 5-10 minutes. O-Chlorophenol (4.6 g) was added portion-wise (no exotherm). Subsequently, a catalytic amount of aluminum chloride was added. The entire solution was then stirred at room temperature overnight.

The next day the solution was heated at reflux for 3 hours, then cooled to room temperature. The methylene chloride was stripped off and the residue was dissolved in ether, then washed with 10% sodium bicarbonate. The ether was evaporated and the residue gas chromatographed. The yield was approximately 1.0 g (11%) of 2-chloro-4-(4,6-dimethyl-2-pyrimidinylthio)-phenol.

A 100 ml, round-bottom flask equipped with stir bar, reflux condenser, drying tube and heating mantle was then charged with a mix of 1.3 g of the 2-chloro-4-(4',6'-dimethyl-2-pyrimidinylthio)phenol, 1.0 g of m-trifluoromethyl benzyl chloride, 0.7 g of potassium carbonate in 20 cubic centimeters (cc) of acetonitrile and heated under reflux for 4 hours, then cooled to room temperature.

The insoluble material was suction-filtered and washed down with a small amount of acetonitrile. The acetonitrile was then stripped off and the oil residue set aside. The residue was dissolved in ether, washed with NaOH (10%) and water, and then dried over magnesium sulfate. A solid residue was obtained from rotary evaporation. The yield was 1.4 g, of 2-[3-chloro-4-(3-trifluoromethylphenylmethoxy)]phenylthio-4,6-dimethyl pyrimidine, m.p. 83°-86° C.

EXAMPLE 2

Preparation of 2-[4-(4-Cyanophenylmethoxy)phenylthio]-4,6-dimethylpyrimidine

A 250 ml. round-bottom flask equipped with a stir bar, addition funnel, drying tube and ice bath was charged with 2.8 g 2-mercapto-4,6-dimethylpyrimidine dissolved in dry methylene chloride. To this was added portion-wise to a stirred solution of the mercapto pyrimidine in methylene chloride, 2.7 g sulfuryl chloride. A rapid exotherm and gas evolution occurred after each addition. The resultant yellow solution was stirred for 5 minutes and then phenol (2.88 g) was added in one portion, producing a rapid exotherm. The resultant clear yellow solution was stirred. After one hour, a precipitate was present. The contents of the flask were diluted with 50 cc hexane and filtered. The yellow solids present were washed with hexane and dried. IR showed this to be a hydrochloride salt. The solid was washed with excess 10% aqueous sodium bicarbonate for 15 minutes in a beaker, then filtered and washed with water. The dried yellow solid was recrystallized from toluene, giving pale yellow prisms, 2 g, (43% yield).

Next, a 100 ml, round-bottom flask equipped with stir bar, reflux condenser, drying tube and heating mantle was charged with a mix of 2 g of 4-(4,6-dimethyl-2-pyrimidinylthio)phenol, 1.7 g of α-bromo-p-tolunitrile, and 1.2 g of potassium carbonate in 20 cc of acetonitrile solution. The mixture was heated under reflux for 3 hours, then cooled to room temperature.

After the reaction was complete, the insoluble material was filtered out and the acetonitrile filtrate was evaporated. A pale yellow solid residue was obtained and recrystallized from toluene and a small amount of cyclohexane. The yield was 1.2 g of the subject compound, m.p. 134°-136° C.

EXAMPLE 3

Preparation of 2-[4(3,5-dichlorophenylmethoxy)phenylthio]-4,6-dimethylpyrimidine A 100 ml, round-bottom flask equipped with stir bar, reflux condenser, drying tube and heating mantle was charged with a mix of 2.0 g 4-(4,6-dimethyl-2-pyrimidinylthio)phenol produced in accordance with paragraph 1 of Example 2, 1.7 g 3,5-dichlorobenzyl chloride, 1.2 g of potassium carbonate and 25 cc of acetonitrile, then heated at reflux overnight.

The reaction mixture was cooled to room temperature, the insoluble material was suction-filtered and the filtrate was rotary evaporated. A yellow solid was obtained. Yield 3.3 g, m.p. 112°-115° C.

EXAMPLE 4

Preparation of Methyl 5-(4,6-dimethyl-2-pyrimidinylthio)-2-phenylmethoxybenzoate A 200 ml round-bottom flask equipped with a nitrogen bubbler, addition funnel and magnetic stir bar was charged with 5.0 g (35.7 mmole) of 2-mercapto-4,6-dimethylpyrimidine in 100 ml methylene chloride (passed through a column of basic alumina). To this was added dropwise over a period of 5 minutes 4.8 g (35.7 mmole) sulfuryl chloride. The solution refluxed. As soon as the last of the sulfuryl chloride had been added, 5.4 g (35.7 mmole) methyl salicylate was added. Then 9.5 g (71.4 mmole) aluminum chloride was very carefully added in portions. After about ½ of the aluminum chloride had been added, each addition caused a vigorous exotherm. The addition was continued more carefully, and was stirred overnight at room temperature.

The mixture was carefully poured into 500 ml saturated sodium bicarbonate. After 1 hour stirring, the pH was approximately 8. Ethyl acetate (300 ml) was added and the mixture was vigorously stirred. It was then filtered. The ethyl acetate layer was separated off, dried over sodium sulfate and stripped, giving 6.5 g yellow oil.

A 25 ml, round-bottom flask equipped with stir bar, condensor, drying tube and heating mantle was charged with 1.0 g of the above phenol, 1.3 g of benzyl bromide, 0.5 g of anhydrous potassium carbonate and 15 ml of acetonitrile and the mixture heated under reflux for 3 hours. The hot mixture was filtered and the filtrate evaporated, giving 2.0 g of yellow oil. The oil was triturated with n-hexane to produce 1.0 g of the title product as an off-white solid.

EXAMPLE 5

Preparation of 2-(4-Butoxy-2-fluorophenylthio)-4,6-dimethylpyrimidine

A 500 ml, round-bottom flask equipped with stir bar, addition funnel, drying tube and external ice bath was charged with 10.0 g of 4,6-dimethyl-2-mercaptopyrimidine in 150 ml of dichloromethane. To this was added 9.9 g of sulfuryl chloride dropwise at 0° C. and stirred for 30 minutes. Subsequently, 8.0 g of 3-fluorophenol was added in one portion with a mild exotherm and stirred at 25° C. for 18 hours. The resultant mixture was diluted with 250 ml hexane and the precipitate collected and neutralized with 10% aqueous sodium bicarbonate in a beaker. The resultant solid was collected, dissolved in 2N aqueous sodium hydroxide solution, the solution washed with diethyl ether and the aqueous phase reacidified to give a precipitate which was collected and dried. The crude product was recrystallized from toluene, giving 5.4 g of desired phenol.

A 100 ml, round-bottom flask equipped with stir bar, condensor, drying tube and heating mantle was charged with 1.5 g of the above phenol, 0.8 g of 1-bromobutane, 1.3 g of anhydrous potassium carbonate and 20 ml of tetrahydrofuran containing a catalytic amount of 1,4,7,10,13,16-hexaoxacyclooctadecane. The resultant mixture was heated under reflux for 18 hours, cooled and poured into 400 ml of water. This mixture was extracted with two 200 ml portions of diethyl ether and the ether was dried over magnesium sulfate. Evaporation gave a crude solid which was purified by silica gel chromatography, eluting with 20% ethyl acetate-hexane. This procedure gave 1.4 g of title product.

EXAMPLE 6

Preparation of 4-(4-Butoxy-3-phenylphenylthio)-4,6-dimethylpyrimidine

A 500 ml, round-bottom flask equipped with stir bar, addition funnel, drying tube and external ice bath was charged with 15.0 g of 4,6-dimethyl-2-mercaptopyrimidine in 150 ml of dichloromethane at 0° C. To this was added 14.4 g of sulfuryl chloride dropwise and the solution was stirred for 20-30 minutes. Subsequently, 18.2 g of 2-phenylphenol was added in one portion with a mild exotherm. The mixture was stirred at 25° C. for 18 hours and the product extracted from the organic solution with 4N aqueous sodium hydroxide. The aqueous solution was acidified to pH 6 and extracted with three 300 ml portions of diethyl ether. Evaporation of the ether gave a crude solid which was purified by silica gel chromatography, eluting with 5% ethyl acetate-dichloromethane to give 14.4 g of the desired phenol.

A 100 ml, round-bottom flask equipped with a stir bar, condensor, drying tube and heating mantle was charged with 3.0 g of the above phenol, 1.3 g of 1-bromobutane, 2.0 g of anhydrous potassium carbonate and 50 ml of acetonitrile and the mixture heated under reflux for 18 hours. The mixture was then cooled, poured into 400 ml of water and extracted with two 200 ml portions of diethyl ether. The ether layers were dried over magnesium sulfate and evaporated giving an impure solid product. This was purified by silica gel chromatography, eluting with 10% ethyl acetate-hexane, producing 2.4 g of the title product.

EXAMPLE 7

Preparation of 2-(4-Butoxy-2-methylphenylthio)-4,6-dimethylpyridimide

A 500 ml, round-bottom flask equipped with stir bar, addition funnel and drying tube was charged with 10.0 g of anhdyrous 4,6-dimethyl-2-mercaptopyrimidine in 150 ml of dichloromethane. To this was added, dropwise, 9.9 g of sulfuryl chloride at 0° C. and the resultant mixture was stirred for 15-20 minutes. Subsequently, 7.7 g of meta-cresol was added portionwise with a mild exotherm and the solution was allowed to stir for 18 hours. The two-phase mixture was diluted with n-hexane to enhance precipitation and the solids collected and neutralized with 10% aqueous sodium bicarbonate in a beaker. The solid was again filtered and purified by silica gel chromatography, eluting with 20% ethyl acetate-hexane, giving 4.9 g of the desired phenol.

A 100 ml, round-bottom flask equipped with stir bar, condensor, drying tube and heating mantle was charged with 1.5 g of the above phenol, 0.8 g of 1-bromobutane, 1.3 g of anhydrous potassium carbonate and 20 ml of anhydrous tetrahydrofuran. The mixture was heated under reflux for 18 hours, cooled and 1.3 g of potassium carbonate and 0.8 g of 1-bromobutane were added and heating continued. Again, after 18 hours, additional potassium carbonate and 1-bromobutane were indicated and after 18 hours under reflux the mixture was cooled, diluted with 300 ml of water and the aqueous solution was extracted twice with 200 ml of diethyl ether. The ether was evaporated and the residue purified by silica gel chromatography eluting with 15% ethyl acetate-hexane, giving 1.7 g of the title product.

EXAMPLE 8

Preparation of 4,6-Dimethyl-2-[(3,5-dimethyl-4-phenylmethoxy)-phenylthio]-pyrimidine A 500 ml, round-bottom flask equipped with stir bar and drying tube was charged with 5.0 g of anhydrous 4,6-dimethyl-2-mercaptopyrimidine in 50 ml of dichloromethane. To this was added, portionwise, sulfuryl chloride generating a mild exotherm. After 5-10 minutes, 2,6-dimethylphenol was added portionwise and the mixture was allowed to stir for several hours.

After being diluted with hexane, the mixture was filtered and the resultant yellow solid was washed with 10% aqueous sodium bicarbonate in a beaker. The solid was collected and washed with water and dried giving 7.7 g of the requisite phenol, m.p. 168°-170° C.

A 100 ml round-bottom flask equipped with stir bar, reflux condenser, drying tube and heating mantle was charged with 2.0 g of the above phenol, 1.0 g of benzyl chloride, 1.1 g of anhydrous potassium carbonate and 25 ml of acetonitrile. The mixture was heated under reflux for 2 days, cooled and suction filtered. The filtrate was evaporated and the residue taken up in diethyl ether. The resultant solution was washed once with 10% aqueous sodium hydroxide to remove unreacted phenol, once with water and the ether layer was evaporated, giving 2.4 g of the title product.

EXAMPLE 9

Preparation of 4,6-Dimethyl-2-[(2,6-dimethyl-4-(3-phenylpropoxy)-phenylthio]pyrimidine A 250 ml, round-bottom flask equipped with stir bar, addition funnel, drying tube and external ice bath was charged with 15.4 g 4,6-dimethyl-2-mercaptopyrimidine in 150 ml of dry dichloroethane. To this was added, dropwise, 14.9 g of sulfuryl chloride resulting in a mild exotherm. After 5-10 minutes, 13.4 g of phenol was added in one portion and stirring continued for 18 hours.

The resultant precipitate was collected and washed with 10% aqueous sodium bicarbonate in a beaker. Subsequently, the solid was collected, washed with water, dried and recrystallized from toluene, giving 24.6 g of the product phenol (80% yield).

A 100 ml round-bottom flask equipped with stir bar, reflux condenser, drying tube and heating mantle was charged with a mixture of 2.0 g of the above phenol, 1.5 g of 3-bromopropylbenzene, 1.1 g of anhydrous potassium carbonate and 25 ml of acetonitrile. This was heated under reflux for 4 hours, cooled and filtered. The filtrate was evaporated and the residue recrystallized from ethanol, giving 1.8 g of the title product, m.p. 92°-95° C.

The times and temperatures at which the process of this invention can be carried out will depend, of course, on specific compounds being produced. In general, however, temperatures ranging from about 0° C. to about 30° C. have been found to be suitable. The time of reaction will vary, depending on temperature and the pressure used, which is normally atmospheric pressure. In general, the time of the reaction for step (a) can vary from about 30 minutes to about one hour. Step (b) can take up to 18 hours or more.

Suitable solvents which can be used in step (a) of the process as described above are the halocarbons in general. Specific solvents which have been found to be useful include methylene chloride and chloroform. The most preferred solvent is methylene chloride.

The function of the sulfuryl chloride used in step (a) is to convert the thiopyrimidine to a sulfenyl chloride.

In the case where halogenated phenols are used as a reactant, the Friedal-Crafts catalyst should be used. Any Friedal-Crafts catalyst can be used in step (b) of the process of the invention to facilitate the reaction of the sulfenyl chloride of the thiopyrimidine with the phenol.

The preferred Friedal-Crafts catalyst is aluminum chloride.

The base used in step (c) of the reaction can be any conventional base, including sodium hydroxide, sodium carbonate, potassium carbonate, and the like. The preferred base is potassium carbonate.

The alkylating agent used in step (c) of the reaction can be of the conventional type. Suitable alkylating agents include m-trifluoromethyl benzyl chloride, α-bromo-p-toluidine, 3,5-dichlorobenzyl chloride and the like. The specific alkylating agent used, will of course, depend upon the final product desired.

Compounds produced in accordance with the process described include:
4,6-dimethyl-2-[2,6-dimethyl-4-(1-phenylethoxy)-phenylthio]pyrimidine;
4,6-dimethyl-2-[2,6-dimethyl-4-(3-phenylpropoxy)-phenylthio]pyrimidine;
4,6-dimethyl-2-[2,6-dimethyl-4-(3-trifluoromethyl-phenylmethoxy)phenylthio]pyrimidine;
4,6-dimethyl-2-[3,5-dimethyl-4-(3-trifluoromethyl-phenylmethoxy)phenylthio]pyrimidine;
2-[4-(2,4-dichlorophenylmethoxy)-3,5-dimethylphenyl-thio]-4,6-dimethylpyrimidine;
4,6-dimethyl-2-[(3,5-dimethyl-4-phenylmethoxy)-phenylthio]pyrimidine;
2-[3-chloro-4-(3-trifluoromethylphenylmethoxy)-phenylthio]-4,6-dimethylpyrimidine;
4,6-dimethyl-2-[4-(3-trifluoromethylphenylmethoxy)-2,3,5,6-tetramethylphenyl]thiopyrimidine;
2-[[4-(2,4-dichlorophenyl)methoxy]-2,3,5,6-tetramethylphenyl]thiopyrimidine;
4,6-dimethyl-2-[3-methyl-4-(2-methylphenoxy)phenyl-thio]pyrimidine;
4,6-dimethyl-2-(4-propoxy-3-methylphenylthio)pyrimidine;
2-[4-(4-cyanophenylmethoxy)phenylthio]-4,6-dimethyl-pyrimidine;
2-[4(3,5-dichlorophenylmethoxy)phenylthio]-4,6-dimethylpyrimidine;
2-(4-butoxy-2-methylphenylthio)-4,6-dimethylpyrimidine;
2-(4-[1-(3,4-dichlorophenyl)ethoxy]-2-methylphenylthio)-4,6-dimethylpyrimidine;
4-(4-butoxy-3-phenylphenylthio)-4,6-dimethylpyrimidine;
4,6-dimethyl-1-2-[3-phenyl-4-(3-trifluoromethylphenyl-methoxy)phenylthio]-pyrimidine; and
2-(4-butoxy-2-fluorophenylthio)-4,6-dimethylpyrimidine.

The process of the invention can be used to produce such herbicidally active phenylthiopyrimidines as are described in commonly assigned Application Ser. Nos. 744,212 and 755,111.

What is claimed is:
1. A process for the preparation of phenylthiopyrimidines which comprises
(a) reacting a thiopyrimidine of the formula

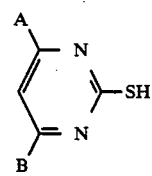

wherein A and B are the same or different and are selected from the group consisting of hydrogen, straight or branched chain alkyl groups having from 1 to about 5 carbon atoms, alkoxy wherein the alkyl group has from 1 to about 5 carbon atoms, mono- or di-alkyl substituted amine wherein the alkyl group has from 1 to about 5 carbon atoms, cyano, COO-alkyl wherein the alkyl group has from 1 to about 5 carbon atoms, trifluoromethyl, chlorine or fluorine; with a sulfuryl chloride chlorinating agent in the presence of a halocarbon solvent to form the sulfenyl chloride of said thiopyrimidine;

(b) reacting said sulfenyl chloride of said thiopyrimidine with phenol or an substituted phenol of the formula

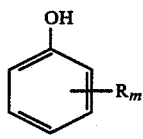

wherein R is hydrogen, alkyl having from 1 to about 5 carbon atoms, halogen, phenyl, cyano, COO-alkyl wherein the alkyl group has from 1 to about 5 carbon atoms, trifluoromethyl or alkoxy wherein the alkyl group has from 1 to about 5 carbon atoms; and m is an integer of from 1 to 4; optionally in the presence of a Friedal-Crafts catalyst, to form a thiopyrimidinylphenol of the formula

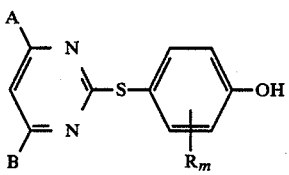

wherein A, B and $R_m$ are as defined above; and (c) reacting said thiopyrimidinylphenol formed in step (b) with base and an alkylating agent of the formula $R'-X_a$ wherein R' is a straight or branched chain alkyl group having from 1 to about 5 carbon atoms, an arylalkyl moiety of the formula

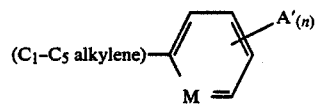

wherein the alkylene group is straight or branched chain; A' is selected from the group consisting of hydrogen, halogen, straight or branched chain alkyl having from 1 to about 5 carbon atoms, nitro, cyano, methoxy, and halogenated alkyl having from 1 to about 5 carbon atoms wherein n is an integer from 1 to 5; M is CH or nitrogen; and $X_a$ is chlorine, bromine or iodine, to form

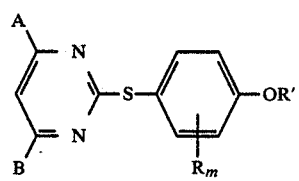

wherein A, B, $R_m$ and R' are as defined above.

2. The method of claim 1 wherein A is methyl, B is methyl, R is hydrogen, R' is cyanophenylmethyl and m is 1.

3. The method of claim 1 wherein A is methyl, B is methyl, R is chloro, R' is 3,5-dichlorophenylmethyl and m is 1.

4. The method of claim 1 wherein A is methyl, B is methyl, R is 2,6-dimethyl, R' is 1-phenylethyl and m is 1.

5. The method of claim 1 wherein A is methyl, B is methyl, R is 2-fluoro, R' is butyl and m is 1.

6. The method of claim 1 wherein said reaction is conducted at a temperature ranging from about 0° to about 30° C.

7. The method of claim 1 wherein said reaction is conducted for a time sufficient to cause completion of the reaction.

8. The method of claim 1 wherein said solvent of step (a) is methylene chloride.

9. The method of claim 1 wherein said Friedal-Crafts catalyst is aluminum chloride.

* * * * *